Figure 1:
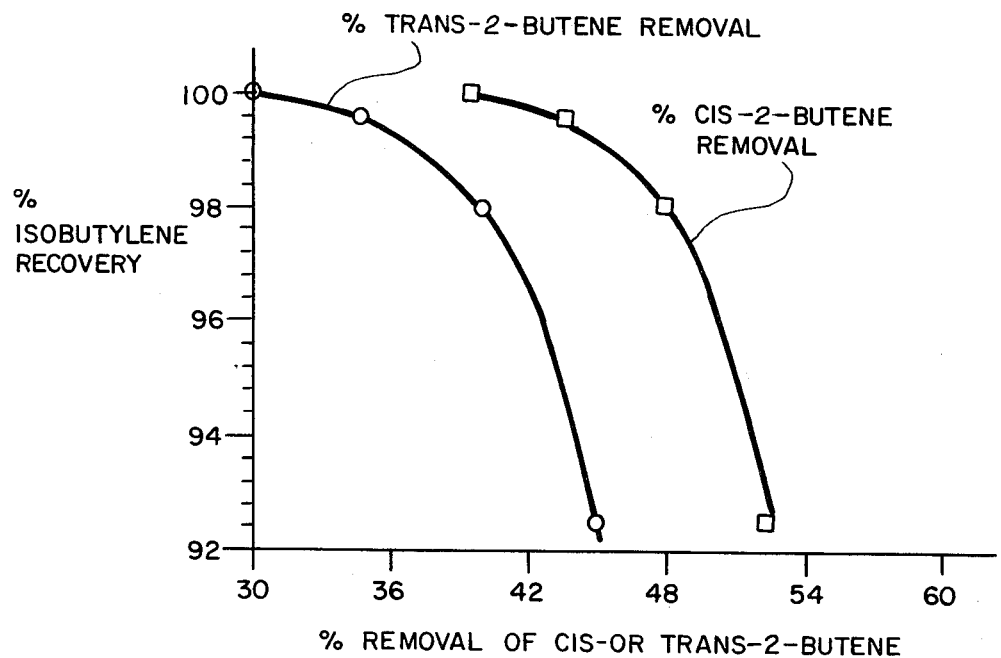
Figure 2:
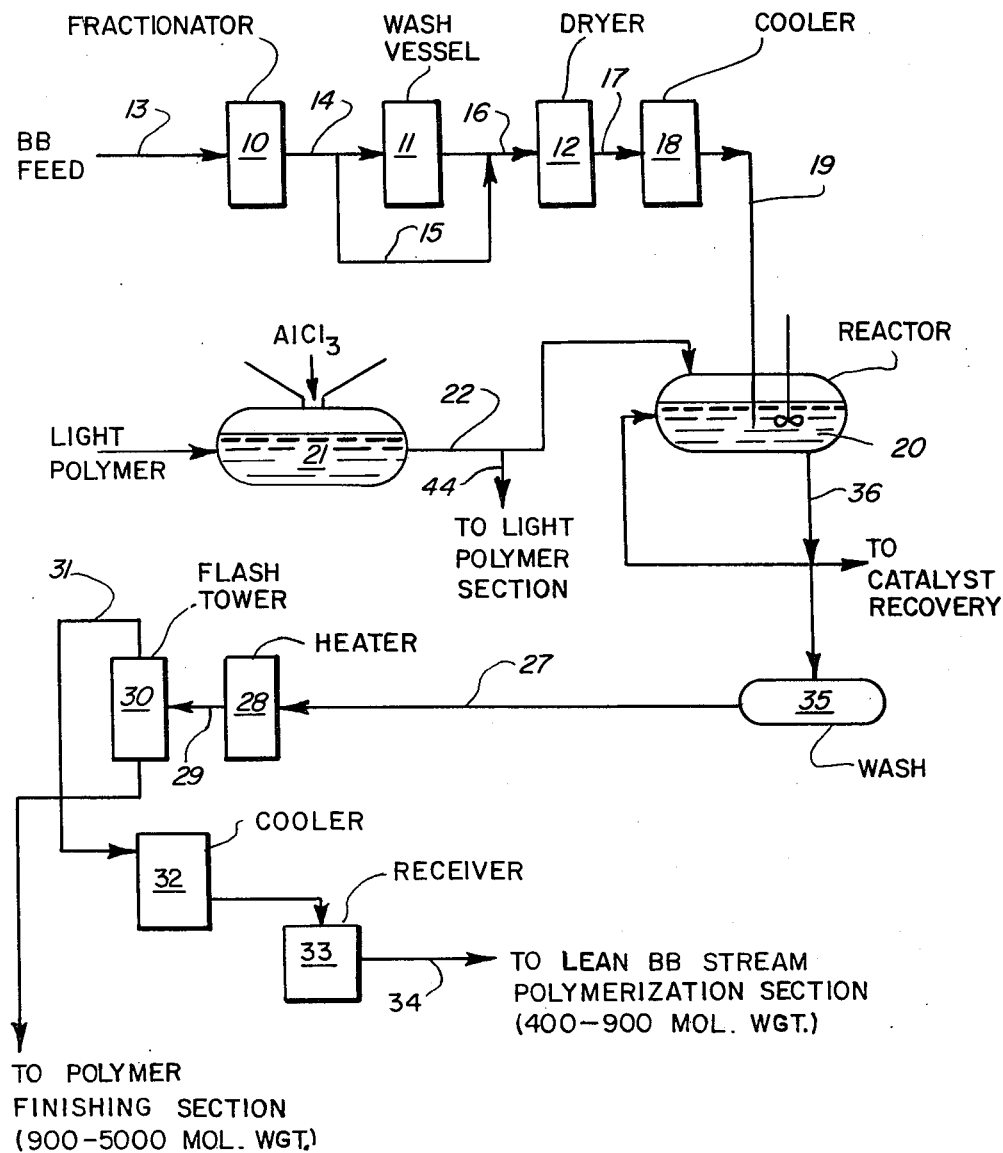
Figure 3:
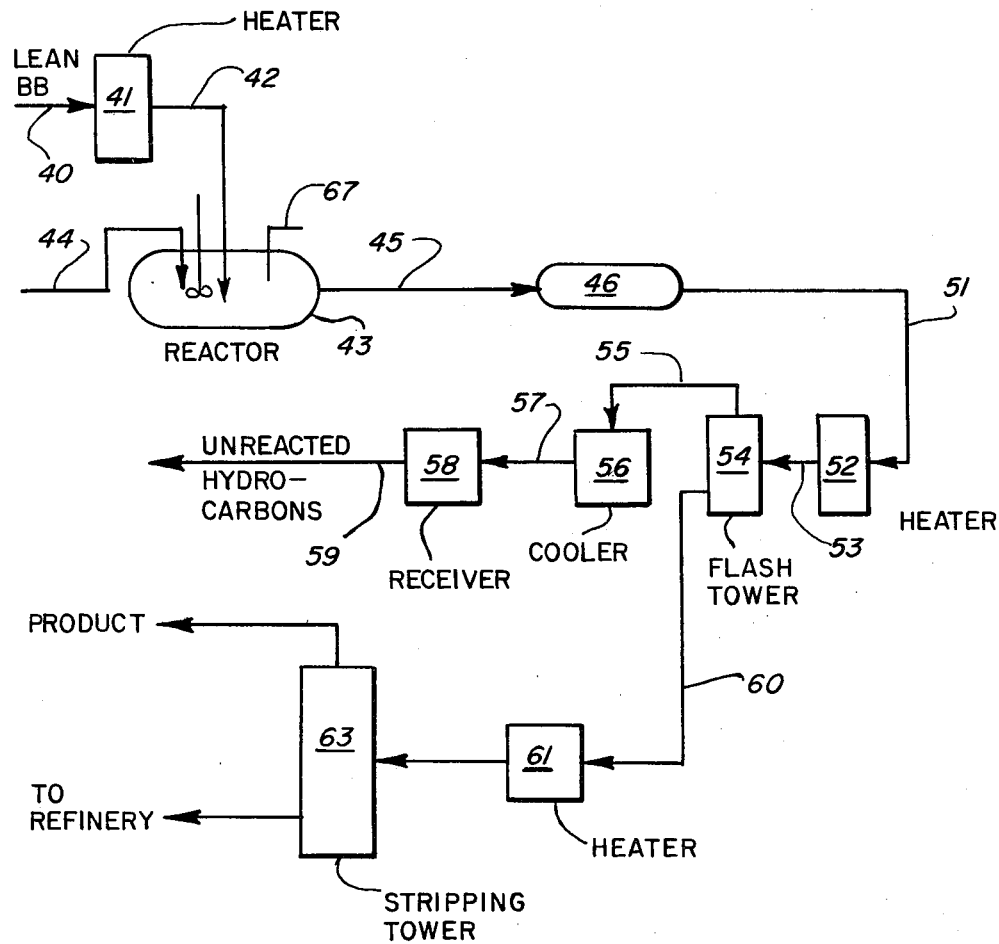

United States Patent [19]

Schammel

[11] Patent Number: 4,465,887
[45] Date of Patent: Aug. 14, 1984

[54] PROCESS FOR PRODUCING BUTYLENE POLYMERS HAVING MOLECULAR WEIGHTS IN THE RANGE OF FROM ABOUT 400 TO 5000 MOLECULAR WEIGHT

[75] Inventor: Wayne P. Schammel, Bartlett, Ill.

[73] Assignee: Standard Oil Company (Indiana), Chicago, Ill.

[21] Appl. No.: 508,334

[22] Filed: Jun. 27, 1983

[51] Int. Cl.$^3$ ............................................. C07C 2/02
[52] U.S. Cl. .................................... 585/517; 585/532
[58] Field of Search ............................... 585/517, 532

[56] References Cited

U.S. PATENT DOCUMENTS 3,763,125 10/1973 Moody et al. ...................... 585/332
3,991,129 11/1976 Daniels ................................ 585/332

Primary Examiner—Curtis R. Davis
Attorney, Agent, or Firm—William C. Clarke; William T. McClain; William H. Magidson

[57] ABSTRACT

Polybutene polymers and polybutene-1 polymers are prepared from a feed stream which has been fractionated to remove no more than about 50 (wt) % of the cis-2-butene originally present.

4 Claims, 3 Drawing Figures

EFFECT OF CIS- AND TRANS-2-BUTENE
REMOVAL ON THE RECOVERY OF ISOBUTYLENE

PROCESS FOR PRODUCING BUTYLENE POLYMERS HAVING MOLECULAR WEIGHTS IN THE RANGE OF FROM ABOUT 400 TO 5000 MOLECULAR WEIGHT

FIELD OF THE INVENTION

This invention relates to novel isobutylene polymers especially suitable for use in caulks, sealants and in oil additives; to novel polybutene-1 polymers especially suitable for use in the alkylation of aromatic hydrocarbons, particularly mononuclear aromatic hydrocarbons; and to an improved method for producing such polymers wherein improved yields of isobutylene polymers are obtained over processes taught heretofore.

It has long been known that normally gaseous olefins can be converted to viscous liquid polymers by means of solid aluminum chloride or by means of liquid aluminum chloride complexes. A well-known and usually used olefin feedstock for such polymerization is a petroleum refinery butane- and butylene-containing stream, referred to as a "B-B stream." The polymerization of a typical butane-butylene refinery stream with aluminum chloride to produce polymers having molecular weights in the range of from about 900 to about 5000 is an established art.

In this process, the primary products, obtained from the polymerization of a typical butane-butylene refinery stream with aluminum chloride by the judicious choice of polymerization temperature and the percent conversion of the isobutylene monomer in such B—B refinery stream, are polymers having molecular weights in the range of from about 900 to about 5000. Polymers having molecular weights of less than about 900, representing from about 10 to about 30 percent of the total polymer, have been used for alkylating mononuclear aromatics, such as benzene, xylenes, and toluene; however, the yield of alkylates from such polymers has resulted in undesirable low yields.

BACKGROUND OF THE INVENTION

This invention relates to an improved method for producing polybutene polymers of molecular weights of from 900 to 5000 and polybutene-1 polymers of molecular weights of from 400 to 1500. Polybutene polymers are defined as liquid polymers of which the monomer is predominantly isobutylene. Polybutene-1 polymers are defined as liquid polymers of which the monomers are isobutylene, butene-1 and cis-2-butene. Trans-2-butene is not defined as a monomer of polybutene-1 although trans-2-butene will react in small amounts as a monomer for polybutene-1 under conditions of high temperature (approximately 65° F.).

Polymers of isobutylene and normal butylenes are known, as are methods of preparing these polymers. It has heretofore been supposed that an advantageous method of making such polymers was to use isobutylene which had been purified by fractionation or chemical means. The object of the purification was to remove substantially all or most of the compounds present which acted to "poison" the polymerization of the isobutylene. Olefins other than isobutylene, of more than two carbon atoms, including butene-2, both cis- and trans-butene-1 were considered as "poisons," as well as organic sulfur containing-compounds, alkyl halides, halogen acids, hydrocarbons of high molecular weight, and in general all sulfur, nitrogen and oxygen compounds which could form stable complexes with Friedel-Crafts catalysts. Another method was to polymerize the isobutylene without prior purification; unreacted hydrocarbons were stripped from the product solution, thus avoiding the need to fractionate or purify by chemical means.

These procedures are taught in U.S. Pat. Nos. 2,296,399; 2,384,916; 2,637,720; 2,657,246; 2,775,577; 2,856,394; 3,501,551; and 3,705,884, which are incorporated herein by reference.

However, fractionation to remove the poisons of cis-2-butene, trans-2-butene and butene-1 has been found to remove substantial amounts of isobutylene from the fractionated stream, thus reducing yield of the isobutylene polymer obtainable from the original feed streams. Fractionation of cis-2-butene and trans-2-butene with or without concurrent fractionation to remove butene-1 results in determinable amounts of isobutylene being returned to the refinery as bottoms of little value. For example, it has been found that in a typical fractionation (using a column of 58 trays) of a feed stream to remove 52.4% cis-2-butene, and 45.0% trans-2-butene, approximately 3.6 times more isobutylene is removed than in fractionating to remove 48.0% cis-2-butene and 40.1% trans-2-butene.

Accordingly, it is an object of the present invention to provide an improved method of preparing isobutylene polymers having molecular weights of from 900 to 5000 from a butene-isobutylene stream suitable for alkylating mononuclear aromatic hydrocarbons. It is another object of this invention to provide an improved method of preparing isobutylene, butene-1, cis-2-butene polymers, known as polybutene-1, polymers, having molecular weights of from 400 to 1500, which polymers are suitable for conversion to sulfonates for motor oil additives. It is another object of this invention to provide an increased supply of butylene polymers from butene-isobutylene feedstocks which are in short supply. Other objects and advantages of the instant invention will become apparent as the detailed description proceeds.

SUMMARY OF THE INVENTION

A process for preparing isobutylene polymers having molecular weights of from 900 to 5000 from a butene-isobutylene stream and isobutylene, butene-1 and cis-2-butene polymers having molecular weights from about 400 to about 1500 wherein the feed stream containing 6–12(wt)% cis-2-butene, 8–15(wt)% trans-2-butene and 8–35(wt)% isobutylene is fractionated to remove no more than about 50(wt)% of said cis-2-butene and wherein isobutylene polymers are polymerized from said fractionated feed stream containing up to about 35(wt)% isobutylene, up to about 12(wt)% of cis-2-butene, up to about 15(wt)% trans-2-butene, about 6 to 14(wt)% butene-1, and polybutene-1 polymers are polymerized from a feed stream containing not more than 5(wt)% isobutylene, wherein the isobutylene polymers are polymerized at a temperature within a range of from about 0° F. to about 75° F. and the isobutylene, butene-1 and cis-2-butene polybutene-1 polymers are polymerized at a temperature within the range of from about 30° C. to about 140° C.

DETAILS OF THE INVENTION

The process of the instant invention relates to a process for preparing isobutylene polymers wherein the feed stream containing up to 12(wt)% of cis-2-butene, up to 15(wt)% trans-2-butene and 8–35(wt)% isobutylene is fractionated to remove no more than about 50(wt)% of the cis-2-butene. While fractionating is considered the most economical way to remove cis-2-butene to desired level, other means, such as use of molecular sieves, preferential solvents, etc., can be used, if suitable. Trans-2-butene is fractionated out only as a result of removing cis-2-butene. From 50 to 60(wt%) of the cis-2-butene and from 60 to 70(wt%) of the trans-2-butene originally present remain in the reactor feed stream.

The process of the instant invention employs a fractionating tower and a two-stage, liquid-phase polymerization system. Aluminum chloride catalyst is added as a slurry in a light molecular weight polymer or it can be dissolved or dispersed in butane. The catalyst is reacted with a fractionated refinery stream containing up to about 35(wt)% isobutylene, hereinafter referred to as a "B—B stream," in a first polymerization after the feed stream from the refinery has been fractionated to remove no more than about 50(wt)% of cis-2-butene content. Reactor temperature of the first reactor is within the range of from about 0° F. to about 75° F. Reactor product is then flashed to obtain a bottoms fraction containing isobutylene polymers, and an overhead fraction containing up to about 5(wt)% isobutylene, and cis-2-butene, trans-2-butene, and butene-1 are removed. Such reactor product is referred to hereafter as a "lean B—B stream." The overhead fraction is thereupon mixed with added aluminum chloride and a promoter. The reactor temperature is within the range of from about 30° F. to 140° F. Reactor product of the second reactor is thereupon flashed to obtain a bottoms fraction containing isobutylene, cis-2-butene and butene-1 polybutene-1 polymers. The overhead is returned to the refinery. A promoter is essential in the second polymerization reaction. Without the presence of a promoter in the second polymerization reactor, no reaction occurs. Typical promoters are isopropyl chloride, t-butyl chloride, water and hydrogen chloride. Concentrations of promoters are in the range of from 100 to 1000 ppm.

In summary, the instant invention comprises a process for preparing isobutylene polymers from a hydrocarbon feed stream comprising up to 12(wt)% cis-2-butene, up to 15(wt)% trans-2-butene and up to 35(wt)% isobutylene, which method comprises: (a) fractionating said feed stream to remove no more than about 50(wt)% of said cis-2-butene; (b) reacting in liquid phase a $C_{4-5}$ hydrocarbon mixture containing isobutylene and an aluminum chloride catalyst at a temperature of from about 0° F. to about 75° F. to polymerize said isobutylene and form a reaction mixture consisting of isobutylene polymers of molecular weight of from 900 to about 5000 and unreacted hydrocarbons including butene-1, cis-2-butene and trans-2-butene; (c) flash distilling said reaction mixture to recover polybutene polymers of molecular weights of from about 900 to about 5000 from unreacted hydrocarbon mixture fraction (ii); (d) reacting in liquid phase said fraction (ii) with a catalyst system consisting of aluminum chloride and a promoter at a temperature of from about 30° F. to about 140° F. to polymerize butylenes in said fraction (ii) and form a reaction product mixture containing butylene polymers; and (e) separating polybutene-1 polymers having molecular weights in the range of about 400–900 from said product mixture. The butylene polymers separated from the product mixture in step (d) are fractionated to obtain polybutene-1 polymer fractions having molecular weights in the range of from about 400 to about 900. The hydrocarbon fraction (ii) in steps (c) and (d) consists of:

|  | Wt. Percent |
|---|---|
| Propane | 0–10 |
| Propylene | 0–10 |
| n-Butane | 0–20 |
| Isobutane | 0–50 |
| Butene-1 | 0–16 |
| cis-2-butene | 0–9 |
| trans-2-butene | 0–10 |
| Isobutylene | 0–5 |
| Pentane | 0–2 |

The invention will be further illustrated by reference to the following specific examples. It should be understood, however, that the detailed expositions of the instant invention, while indicating preferred embodiments, are given by way of illustration only, since various changes and modifications within the spirit and scope of the invention will become apparent to those skilled in the art from this detailed description.

EXAMPLE I

Fractionation to remove the poisons of cis-2-butene, trans-2-butene and butene-1 has been found to remove substantial amounts of isobutylene from the fractionated stream, which amounts are typically returned to refinery "slop" streams, thus reducing yield of isobutylene polymer from the original feed stream.

A typical feed stream was fractionated in a 58-tray fractionating tower. Tower overhead product was further processed to prepare isobutylene polymer. Tower bottoms product was returned to the refinery to be included in the "slop" streams. Tower feed analysis was as follows:

| Feed Analysis | (wt) % |
|---|---|
| Propane | 5.0 |
| Propylene | 5.0 |
| Isobutane | 29.9 |
| n-Butane | 16.9 |
| Butene-1 | 9.0 |
| Isobutylene | 10.9 |
| trans-2-Butene | 10.9 |
| cis-2-Butene | 8.0 |
| Isopentane | 5.0 |
| 1,3-Butadiene | 0.5 |

The tower was operated to remove 45.0 (wt)% trans-2-butene and 52.4 (wt)% cis-2-butene. Operating conditions and results were as follows:

| Operating Conditions | | | |
|---|---|---|---|
| Trays | 58 | Feed Pres., psia | 160 |
| Bottoms Temp °F. | 187.9 | Feed Temp °F. | 159 |
| Bottoms Pres., psia | 154 | Ovhd Temp °F. | 151 |
| Bottoms Withdrawal | | Ovhd Pres., psia | 148 |
| - % of Feed Rate | 23.2 | Feed Rate | |
| - lbs/hr | 51,511 | - lbs/hr | 222,017 |
| - Moles/hr | 864 | - Moles/hr | 3969.2 |
| | | - Temp °F. | 159 |
| Operating Results | | | |
| trans-2-Butene Removed - (To Waste) - (wt) % of Orig. Feed | | 45.0 | |
| cis-2-Butene Removed - (To Waste) - (wt) % of Orig. Feed | | 52.4 | |

-continued

| | |
|---|---|
| Isobutylene Removed - (To Waste) - (wt) % of Orig. Feed | 7.49 |
| Isobutylene Polymerized - (wt) % of Orig. Feed | 92.51 |

Tower product analyses were as follows:

| | Tower Product Analyses | |
|---|---|---|
| | Tower Overhead To Polymer Unit (wt) % | Tower Bottoms To Waste (wt) % |
| Propane | 15.0 | 0.0 |
| Propylene | 15.0 | 0.0 |
| Isobutane | 37.0 | 4.1 |
| n-Butane | 12.6 | 27.6 |
| Butene-1 | 10.2 | 4.0 |
| Isobutylene | 12.9 | 3.6 |
| trans-2-Butene | 6.8 | 19.4 |
| cis-2-Butene | 4.7 | 18.1 |
| Isopentane | 0.0 | 21.2 |

EXAMPLES II-IV

Operating conditions (the bottoms temperature and bottoms withdrawal rate) on the tower were changed successively in Examples II-IV to limit amounts removed of cis-2-butene and trans-2-butene. Other conditions were the same as in Example I. Operating conditions and results were as follows:

| Example | II | III | IV |
|---|---|---|---|
| Operating Conditions | | | |
| Tower Bottoms to Waste | | | |
| - lbs/hr | 43,300 | 37,875 | 33,584 |
| - Moles/hr | 720 | 625 | 550 |
| - Temp, °F. | 191.8 | 194.4 | 196.6 |
| - Analysis (wt) % | | | |
| Propane | — | — | — |
| Propylene | — | — | — |
| Isobutane | 1.1 | 0.3 | 0.1 |
| n-Butane | 30.6 | 29.1 | 26.3 |
| Butene-1 | 1.6 | 0.5 | 0.2 |
| Isobutylene | 1.2 | 0.3 | 0.1 |
| trans-2-Butene | 20.6 | 20.5 | 19.8 |
| cis-2-Butene | 19.7 | 20.6 | 21.1 |
| Isopentane | 25.2 | 28.8 | 32.4 |
| - Withdrawal Rate - % of Feed | 19.5 | — | — |
| Operating Results (wt) % of Orig. Feed | | | |
| trans-2-Butene Removed (To Waste) | 40.1 | 34.9 | 29.9 |
| cis-2-Butene Removed (To Waste) | 48.0 | 43.8 | 39.8 |
| Isobutylene Removed (To Waste) | 2.1 | 0.5 | 0.2 |
| Isobutylene Polymerized | 97.9 | 99.5 | 99.8 |

The above data in Examples I-IV were plotted as in FIG. I. FIG. I indicates that recovery of isobutylene decreases rapidly from approximately 100% if removal of trans-2-butene is greater than about 45 (wt)% and removal of cis-2-butene is greater than about 52 (wt)% of a feed stream containing about 11-13 (wt)% of isobutylene.

EXAMPLE V

A feed stream containing 12(wt)% cis-2-butene was fractionated in a 58-tray fractionating tower to remove 44.5(wt)% of the cis-2-butene present. Recovery of isobutylene to be polymerized was consistent with data in FIG. 1 wherein cis-2-butene content in the feed stream was 8(wt)%. Referring to FIG. 1, the data indicate greater recovery of isobutylene can be obtained with up to about 50(wt)% removal of the cis-2-butene present, wherein the feed stream can contain up to 12(wt)% of cis-2-butene.

Tower overhead was processed to prepare isobutylene polymer. Tower bottoms product was returned to the refinery to be included in the "slop" streams. Tower feed analysis was as follows:

| Feed Analysis | (wt) % |
|---|---|
| Propane | 5.0 |
| Propylene | 5.0 |
| Isobutane | 26.0 |
| n-Butane | 17.0 |
| Butene-1 | 9.0 |
| Isobutylene | 11.0 |
| trans-2-Butene | 10.0 |
| cis-2-Butene | 12.0 |
| Isopentane | 5.0 |
| 1,3-Butadiene | — |

The tower was operated to remove 44.5(wt)% cis-2-butene and 37.1(wt)% trans-2-butene. Operating conditions and results were as follows:

| Operating Conditions | | | |
|---|---|---|---|
| Trays | 58 | Feed Pres., psia | 160 |
| Bottoms Temp. °F. | 1921 | Feed Temp. °F. | 159 |
| Bottoms Pres., psia | 154 | Ovhd Temp. °F. | 143 |
| Bottoms Withdrawal | | Ovhd Pres., psia | 148 |
| - % of Feed Rate | 20.0 | Feed Rate | |
| - lbs/hr | 43,135 | - lbs/hr | 216,143 |
| - Moles/hr | 720 | - Moles/hr | 3,869 |
| | | - Temp °F. | 159 |
| Operating Results | | | |
| trans-2-Butene Removed - (To Waste) - (wt) % of Orig. Feed | 37.1 | | |
| cis-2-Butene Removed - (To Waste) - (wt) % of Orig. Feed | 44.5 | | |
| Isobutylene Removed - (To Waste) - (wt) % of Orig. Feed | 1.7 | | |
| Isobutylene Polymerized - (wt) % of Orig. Feed | 98.3 | | |

Tower product analyses were as follows:

| | Tower Product Analyses | |
|---|---|---|
| | Tower Overhead To Polymer Unit (wt) % | Tower Bottoms To Waste (wt) % |
| Propane | } 12.5 | 0.0 |
| Propylene | | 0.0 |
| Isobutane | 32.4 | 0.2 |
| n-Butane | 14.4 | 27.3 |
| 1-Butene | 10.8 | 2.0 |
| Isobutylene | 13.5 | 0.9 |
| trans-2-Butene | 7.9 | 18.6 |
| cis-2-Butene | 8.3 | 26.7 |
| Isopentane | 0.2 | 24.3 |

The above tower overhead product was polymerized at a temperature of 56° F. using $AlCl_3$ catalyst to yield isobutylene polymer of 950 molecular weight.

The isobutylene polymer was then flashed to recover an isobutylene stream containing about 2(wt)% isobutylene, 9.3(wt)% cis-2-butene and 8.9(wt)% trans-2-butene as a lean B—B stream.

The lean B—B stream was thereupon polymerized using isopropyl chloride as an initiator at a temperature of 140° F. Other conditions were: 0.4(wt)% $AlCl_3$; 1-hr.

residence time. Resulting polybutene-1 polymer had a molecular weight of 580.

The invention will be more fully described from the following detailed description of a specific example read in conjunction with the accompanying drawings, which form a part of this specification, wherein:

FIG. II is a schematic flow diagram of a first polymerization section for the polymerization of a B—B stream, and FIG. III is a schematic flow diagram of a second polymerization section for the polymerization of a lean B—B stream.

While the invention is applicable to liquid-phase polymerization of mixtures of isobutylene and normal butylenes, it is primarily directed to the polymerization of mixtures of isobutylene and normal butylenes associated with butanes in the B—B stream. In this example, the charging stock is a B—B refinery stream, having the following approximate composition:

|  | Percent |
| --- | --- |
| Propane | 5.0 |
| Propylene | 5.0 |
| n-Butane | 16.9 |
| Isobutane | 29.9 |
| Butene-1 | 9.0 |
| Cis-2-butene | 8.0 |
| Trans-2-butene | 10.0 |
| Isobutylene | 10.9 |
| Pentanes | 5.0 |

A two-section process for the polymerization of a refinery B—B stream is described hereinafter.

FIRST POLYMERIZATION SECTION

Referring to FIG. II, charging B—B feedstock from fractionator 10 is optionally washed in vessel 11 with about a 10% NaOH solution to remove mercaptan sulfur, if present, from the feed and then passed through a fractionation tower or a drier 12 to remove water. The dried feedstock is then passed through line 17 and one or more heat exchangers or coolers 18 to cool the feed stream to a temperature of about 0° F. to 65° F., suitably about 35° F. The cooled feed stream is then passed via line 19 to the bottom of reactor 20 and charged thereinto.

The aluminum chloride catalyst, AlCl₃, is added via a hopper to a vessel 21 containing light polybutene polymer. The resulting slurry is then added to the reactor continuously via line 22. The aluminum chloride is in the form of a fine powder when added to the light polybutene polymer. The light polybutene polymer has been previously dried over calcium chloride before use.

Product effluent from reactor 20, consisting of polymerized isobutylene, aluminum chloride-hydrocarbon complex, and unreacted hydrocarbons, such as normal butylenes and butanes, is passed via line 36 to a wash vessel 35. The purpose of the wash is to remove all residual amounts of aluminum chloride catalyst and yield a pure organic product mixture.

The product from the wash, consisting of isobutylene polymers and unreacted hydrocarbons, comprising chiefly normal butylenes and butanes, is passed via line 27, through heater 28, and line 29 to flash tower 30 operated at a pressure of about 80-100 psig with a top temperature of about 120°-170° F. and a bottom temperature of about 290°-310° F. by means of a heater.

In flash tower 30, unreacted hydrocarbons, chiefly normal butylenes and butanes, are taken overhead through line 31, condensed in cooler 32, and collected in receiver 33. This condensed overhead collected in receiver 33, hereinafter referred to as "lean B—B stream," having the following approximate composition:

|  | Percent |
| --- | --- |
| Propane | 8.1 |
| Propylene | 8.1 |
| n-Butane | 14.5 |
| Isobutane | 42.5 |
| Butene-1 | 11.7 |
| cis-2-butene | 5.4 |
| trans-2-butene | 7.8 |
| Isobutylene | 2.0 |
| Pentane | 0.0 | is removed from receiver 33, via valved line 34, and polymerized in a second polymerization section, as hereinafter described.

Isobutylene polymers are removed from the bottom of flash tower 30, and fractionated into polymers of desired molecular weights by well-known means.

SECOND POLYMERIZATION SECTION

Referring to FIG. III, lean B—B stream from receiver 33 (FIG. 1) is passed via valved line 40, through heat exchanger 41, wherein it is heated to a temperature of from about 25° F. to about 300° F., and via line 42 to the bottom of reactor 43.

Aluminum chloride can be added to the reactor as a slurry prepared as hereinbefore described. Alternatively, it may be dissolved in hot butane and added in this manner. It is then passed via line 44 into reactor 43, wherein it is mixed with the lean B—B stream feed by means of suitable agitator means, such as a stirrer. A promoter, isopropyl chloride, is added to reactor 43 by line 67. A temperature of about 30°-140° F. is maintained in reactor 43 by suitable refrigeration means.

Product effluent from reactor 43, consisting of polymerized normal butylenes, aluminum chloride-hydrocarbon complex, promoter and unreacted hydrocarbons, such as normal butylenes and butanes, is passed via line 45 to wash vessel 46 to remove catalyst, as described previously. The promoter is also removed in the wash vessel 46.

The organic product from the wash vessel 46, consisting of normal butylene polymers and unreacted hydrocarbons, is passed via line 51, through heater 52, and line 53 to flash tower 54 operated at a pressure of about 80-100 psig with a top temperature of about 120°-170° F. and a bottom temperature of about 290°-310° F.

In flash tower 54, unreacted hydrocarbons, chiefly butanes, are taken overhead through line 55, condensed in cooler 56, and collected in receiver 58.

The overhead from flash tower 54, having the following approximate composition:

|  | Percent |
| --- | --- |
| Propane | 10.9 |
| Propylene | 2.7 |
| n-Butane | 19.8 |
| Isobutane | 58.0 |
| Butene-1 | 2.0 |
| cis-2-butene | 1.1 |
| trans-2-butene | 5.5 |
| Isobutylene | 0.0 |

| | Percent |
|---|---|
| Pentane | 0.0 | is removed from receiver 58 via line 59.

From the bottom of flash tower 54, the normal butylene polymers pass via line 60 through heater 61 to a polymer fractionating stripping tower 63 where the polybutene-1 polymer is fractionated into polymers of desired molecular weights by well-known means.

The herein described invention provides a process for increasing the yields of lower molecular weight normal butylene polymers, without decreasing the yields of higher molecular weight isobutylene polymers. Further, fractions of the lower molecular weight normal butylene polymer can be varied by controlling the reaction temperature of the second polymerization section reactor. The lower molecular weight normal butylene polymers, essentially free of isobutylene polymers, have greater thermal stability than the lower molecular weight polybutenes heretofore produced as a by-product stream from a single stage B—B stream polymerization process.

Percentages herein given are weight percentages unless otherwise stated.

We claim:

1. A process for preparing isobutylene polymers from a hydrocarbon feed stream comprising a $C_4$–$C_5$ hydrocarbon mixture containing up to 12(wt)% cis-2-butene, up to 15(wt)% trans-2-butene and up to 35% (wt)% isobutylene, which method comprises:
   (a) fractionating said feed stream comprising said $C_4$–$C_5$ hydrocarbon mixture to remove no more than about 50(wt)% of said cis-2-butene of said $C_4$–$C_5$ hydrocarbon mixture;
   (b) reacting in liquid phase the overhead fraction from said fractionating of said feed stream comprising said $C_4$–$C_5$ hydrocarbon mixture containing isobutylene and an aluminum chloride catalyst at a temperature of from about 0° F. to about 75° F. to polymerize said isobutylene and form a reaction mixture consisting of isobutylene polymers of molecular weight of from 900 to about 5000 and unreacted hydrocarbons including butene-1, cis-2-butene and trans-2-butene;
   (c) flash distilling said reaction mixture to recover polybutene polymers of molecular weights of from about 900 to about 5000 from unreacted hydrocarbon mixture fraction (ii);
   (d) reacting in liquid phase said fraction (ii) with a catalyst system consisting of aluminum chloride and a promoter at a temperature of from about 30° F. to about 140° F. to polymerize butylenes in said fraction (ii) and form a reaction product mixture containing butylene polymers; and
   (e) separating polybutene-1 polymers having the molecular weights in the range of about 400–900 from said product mixture.

2. The process of claim 1 wherein the butylene polymers separated from the product mixture in step (d) are fractionated to obtain polybutene-1 polymer fractions having molecular weights in the range of from about 400 to about 900.

3. The process of claim 1 wherein the hydrocarbon fraction (ii) in steps (c) and (d) consists of:

| | Percent |
|---|---|
| Propane | 0–10 |
| Propylene | 0–10 |
| n-Butane | 0–20 |
| Isobutane | 0–50 |
| Butene-1 | 0–16 |
| cis-2-butene | 0–9 |
| trans-2-butene | 0–10 |
| Isobutylene | 0–5 |
| Pentane | 0–2 |

4. The process of claim 1 wherein said promoter is selected from the group consisting of isopropyl chloride, t-butyl chloride, hydrogen chloride and water.

* * * * *